US006299736B1

United States Patent
Windhorst et al.

(10) Patent No.: US 6,299,736 B1
(45) Date of Patent: Oct. 9, 2001

(54) PROCESS FOR RECOVERING γ-BUTYROLACTONE FROM A MIXTURE OF HEAVY ORGANICS

(75) Inventors: Kenneth A. Windhorst, Pampa; H. Robert Gerberich, Corpus Christi; Deborah A. Sitz, Panhandle; Nicole Garrett-Wallace, Pampa; R. Jay Warner, Corpus Christi, all of TX (US)

(73) Assignee: Celanese International Corporation, Dallas, TX (US)

( * ) Notice: Subject to any disclaimer, the term of this patent is extended or adjusted under 35 U.S.C. 154(b) by 0 days.

(21) Appl. No.: 09/333,587

(22) Filed: Jun. 15, 1999

(51) Int. Cl.[7] .............................. B01D 3/36; C07D 307/02
(52) U.S. Cl. .................................. 203/68; 203/70; 203/78; 549/295; 549/325
(58) Field of Search .................................. 203/68, 70, 73, 203/74, 77, 80, 98, 78; 549/295, 325, 326, 509

(56) References Cited

U.S. PATENT DOCUMENTS 2,875,213 * 2/1959 Ulvild et al. ........................ 549/295
4,175,089 * 11/1979 Heiba et al. ........................ 549/295
4,851,085 * 7/1989 De Thomas ........................ 549/295
5,319,111 * 6/1994 Zimmermann et al. ............. 549/325

FOREIGN PATENT DOCUMENTS

57016963 * 4/1982 (JP) .
60001142 * 6/1983 (JP) .
60109532 * 6/1985 (JP) .

OTHER PUBLICATIONS

Smogorzheoskaya et al Moscow USSR Zh. Prike–Khim 1989 62(8) Russian Journal.*

* cited by examiner

*Primary Examiner*—Virginia Manoharan
(74) *Attorney, Agent, or Firm*—M. Susan Spiering

(57) ABSTRACT

Gamma-Butyrolactone (GBL) is recovered from a mixture containing GBL and other heavy organics by a process of azeotropic distillation in the presence of a $C_{8-C\,10}$ hydrocarbon as an azeotroping agent, wherein an azeotrope of GBL and the hydrocarbon is obtained as a distillate, which forms immiscible GBL-rich and hydrocarbon-rich phases, and the hydrocarbon-rich phase is decanted or isolated from the GBL-rich phase. By this process GBL can be efficiently separated from a large proportion of various compounds having boiling points close to that of GBL, e.g., the methyl-γ-butyrolactones (MeGBL's).

14 Claims, 1 Drawing Sheet

PROCESS FOR RECOVERING γ-BUTYROLACTONE FROM A MIXTURE OF HEAVY ORGANICS

BACKGROUND OF THE INVENTION

1. Field of the Invention

This invention relates to an improved process for recovering gamma-butyrolactone (γ-butyrolactone) from a mixture of heavy organics by means of azeotropic distillation.

2. Description of the Related Art

γ-Butyrolactone (GBL) is a commodity of commerce useful in various applications such as a chemical intermediate, e.g., in the preparation of butyric compounds and polyvinylpyrrolidone, a solvent for various polymers, e.g., acrylate and styrene polymers, and in specialty products such as paint removers, textile assistants and drilling oils.

In a number of commercial processes resulting in the synthesis of GBL, e.g., the liquid phase oxidation of butane with molecular oxygen and the reaction of acetylene and formaldehyde using Reppe chemistry, the GBL is obtained in admixture with other relatively heavy, i.e., high boiling organic compounds, several of which have boiling points very close to GBL, e.g., the methyl-γ-butyrolactones (MeGBL's). In view of this, it is difficult to recover GBL in sufficiently high purity from these other heavy organics without incurring prohibitively high energy and equipment costs so that in many instances, mixtures of heavy organics containing a relatively high percentage of GBL are burned for fuel rather than treated to recover the GBL. Thus, any expedient which is effective in rendering the economic recovery of GBL in high purity from mixtures with heavy organics, would be very desirable.

U.S. Pat. No. 2,875,213 issued Feb. 24, 1959 to Ulvild et al., discloses the recovery of GBL from a distillation fraction of the product of liquid phase oxidation of n-butane, comprising a major proportion of GBL and a minor proportion of glycol esters having boiling points close to that of GBL, by solvent extraction with a dual solvent of water and a liquid aliphatic hydrocarbon, e.g., n-hexane, to obtain aqueous and hydrocarbon phases, and obtaining GBL of high purity from the aqueous phase by distillation.

U.S. Pat. No. 4,851,085, issued Jul. 25, 1989 to De Thomas, discloses a process of treating GBL of at least 95% purity with a strong acid, e.g., a mineral acid or acidic ion exchange resin, to remove color forming impurities for product stabilization.

U.S. Pat. No. 5,319,111 issued Jun. 7, 1994 to Zimmermann et al. teaches a process for the preparation of tetrahydrofuran and GBL from the product of the hydrogenation of maleic acid, succinic acid, maleic anhydride, succinic anhydride and/or fumaric acid, by treating the crude hydrogenation product with a protic acid, e.g., a mineral acid or cation exchange resin, and isolating pure tetrafuran and GBL from the reaction mixture by distillation.

BRIEF SUMMARY OF THE INVENTION

In accordance with this invention, γ-butyrolactone (GBL) is recovered from a mixture containing GBL and other heavy organics by a process of azeotropic distillation in the presence of a $C_{8-C10}$ hydrocarbon as an azeotroping agent. An azeotrope of GBL and the hydrocarbon is obtained as a distillate, which forms immiscible GBL-rich and hydrocarbon-rich phases. The hydrocarbon-rich phase is then decanted from the GBL-rich phase. By this process, GBL can be efficiently separated from a large proportion of various compounds having boiling points close to that of GBL, e.g., the methyl-γ-butyrolactones (MeGBL's).

BRIEF DESCRIPTION OF THE DRAWING

The drawing illustrates a process for the production of GBL from a residue obtained in the purification of the products of the liquid phase oxidation of n-butane with molecular oxygen, utilizing the azeotropic distillation process of the invention.

DETAILED DESCRIPTION OF THE INVENTION

Figure 1:
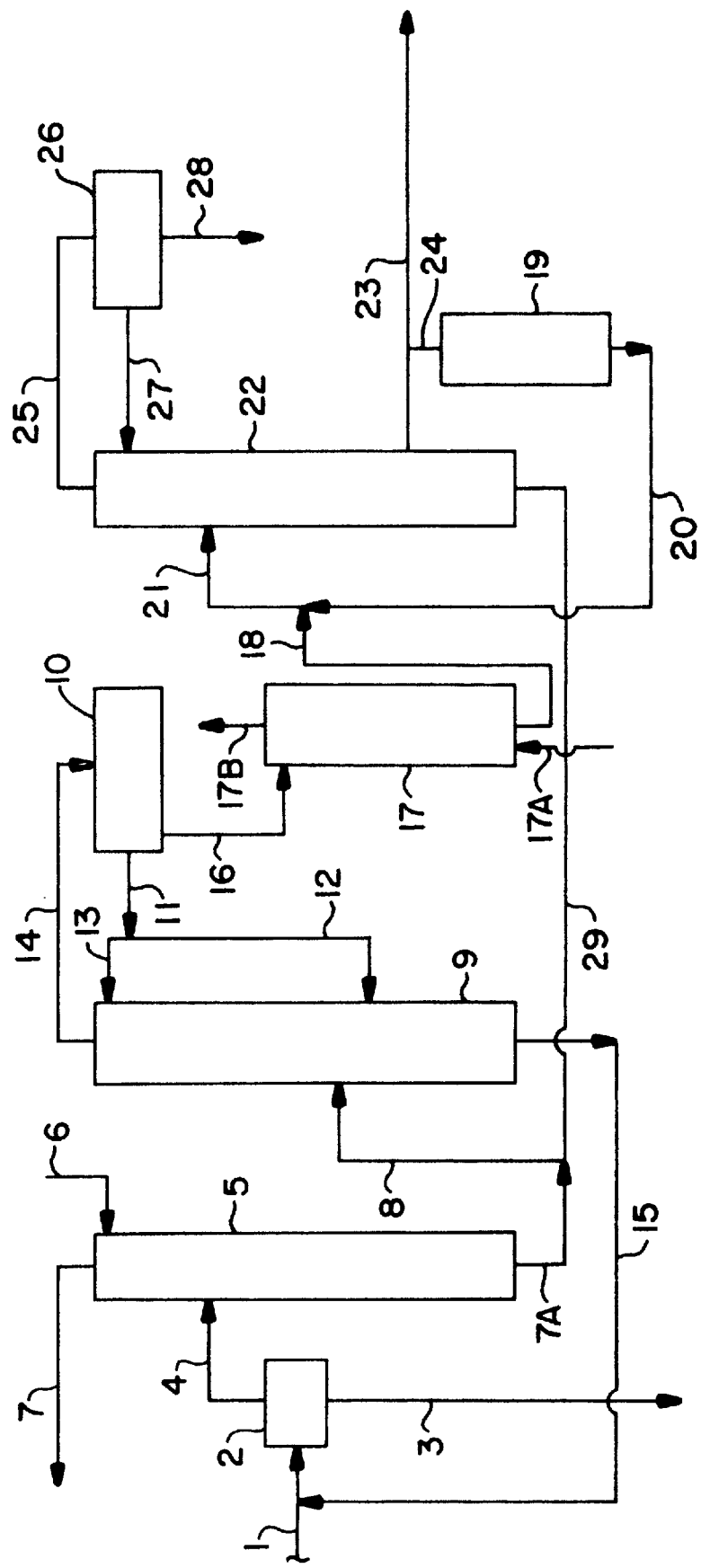

In an embodiment the feed mixture subjected to the azeotropic distillation of this invention will contain about 1 to about 99 wt. % of GBL and at least about 1 wt. % of other relatively heavy organic compounds. Preferably the feed mixture will contain about 10 to about 80 wt. % of other heavy organic compounds, having an atmospheric boiling point of at least about 130° C., preferably about 150° C. to about 250° C. The organic compounds in the feed mixture may include, for example, about 0.1 to about 50 wt. % of MeGBL's and/or about 0.1 to about 50 wt. % of esters having boiling points within the foregoing ranges. All of the foregoing weight percents are based on the total weight of the mixture fed to the azeotropic distillation unit.

The $C_{8-C10}$ hydrocarbon azeotroping agent may be, for example, n-octane, n-nonane or n-decane, and is preferably n-octane. The weight ratio of azeotroping agent to the GBL-containing mixture fed to the azeotropic distillation unit may be, for example, about 1 to about 99 wt. %, preferably about 5 to about 30 wt. %. The azeotropic distillation unit is preferably a column containing, for example, about 10 to about 100 trays which operates at continuous steady state at a pressure of, for example, about 10 to about 100 psia, a reboiler temperature of, for example, about 150 to about 300° C. and a top tray temperature of, for example, about 100 to about 200° C.

The feed mixture flows into the azeotrope distillation column at an intermediate tray and hydrocarbon azeotroping agent composed mainly of recycled hydrocarbon as discussed hereinafter plus any makeup hydrocarbon necessary to maintain the amount in the column at a desired level, is fed to the column at a tray below the feed point, e.g. about 1 to 50 trays below the feed point, which allows for good physical contact between the feed and the azeotroping hydrocarbon. A vaporous azeotrope of GBL and hydrocarbon azeotroping agent is withdrawn from the top of the column and is condensed into a distillate containing immiscible GBL-rich and hydrocarbon-rich phases which are separated in a decanter, preferably using chilled water as a coolant. Most of the upper hydrocarbon-rich phase in the decanter is recycled to the azeotroping column at a tray below the feed point as discussed, and a reflux amount of hydrocarbon only large enough to maintain liquid on the top trays of the column is fed to the top of the column. The lower GBL-rich liquid phase in the decanter is crude GBL containing, for example, about 5 to about 98 wt. % of GBL. Since the solubility of hydrocarbon in the GBL-rich phase increases with increasing temperature, in the case of n-octane rising from about 1.9 wt. % at 12° C. to about 2.9 wt. % at 40° C., the temperature of the liquid in the decanter should be kept as low as practicable, e.g. from about 0 to about 20° C., to avoid the loss of hydrocarbon downstream from the azeotroping column.

The crude GBL from the azeotroping column is found to contain only a minor percentage of the MeGBL's present in the feed to the azeotroping column, e.g. about 10 to about 50 wt. %. This is an unexpected advantage of the process of this invention since the MeGBL's, considered a serious impurity in commercial GBL, have boiling points similar to that of GBL, namely about 204° C.

In many instances, the GBL subjected to further purification, heating and storage downstream from the azeotropic distillation unit develops an undesirable color which can be traced to the presence of unsaturated impurities in the crude GBL obtained from the distillation. Thus, in accordance with another aspect of the invention, the crude GBL obtained from the azeotropic distillation unit is subjected to a hydrogenation treatment to eliminate or reduce the unsaturation of the unsaturated impurities present in the crude GBL. The hydrogenation may be carried out, for example, in a pipe reactor packed with a catalyst effective for the hydrogenation of carbon-carbon double bonds (C=C) as are well known in the art. A particularly effective catalyst is palladium, e.g. supported on carbon. The hydrogenation reaction may be carried out at a hydrogen pressure of, for example, about 1 to about 500 psig and a temperature of, for example, about 100 to about 300° C. at a residence time sufficient to eliminate or reduce the unsaturated impurities to a sufficiently low level.

Whether the crude GBL from the azeotropic distillation unit is subjected to a hydrogenation treatment or not, it is generally too impure for commercial use, i.e. contains a sufficiently large amount of impurities having lower and higher boiling points than GBL such as organic acids, ethylene glycol diacetate (EGDA) and 2,5-hexanedione, to cause interference with the effectiveness of the GBL for several of its applications. It is therefore another aspect of the invention to subject the crude GBL, after the hydrogenation step if such hydrogenation is deemed necessary or desirable, to a purification treatment such as vacuum distillation as a finishing treatnent for the purpose of removing such impurities. The vacuum distillation intended to produce a GBL of high purity, may be carried out a pressure of, for example, about 10 to about 700 mm Hg absolute while maintaining the reboiler temperature close to about 150° C. and a top end distillate temperature of about 50 to about 150° C., in a column containing, for example, about 10 to about 100 trays. Preferably, the feed (crude GBL) is introduced at a point above the midpoint of the column and the product is withdrawn as a vapor sidestream from a point below the midpoint several trays above the reboiler to remove traces of heavy ends, i.e., impurities having boiling points higher than that of GBL, from the product. The sidestrean product generally has a GBL content of over 99 wt. % and lighter impurities, i.e. having boiling points below that of GBL, such as lighter organic acids, EGDA and 2,5-hexanedione, are removed in the overhead distillate.

Despite the relatively high purity of the GBL product from the purification or finishing column, it has been found that such product may still contain various high boiling esters which may interfere with the use of GBL in certain applications, e.g. in the electronics and pharmaceutical industries. In accordance with another aspect of the invention, all or part of the product from the finishing column may be subjected to hydrolysis conditions to hydrolyze the high boiling esters contained therein and is then subjected to distillation to remove the acid and alcohol products of hydrolysis. One method of accomplishing this is to add a small amount, e.g. about 1 to 3 wt. % of water to at least part of the side-stream product of the finishing column, then contact the water-containing product stream with an acidic hydrolysis catalyst, and finally recycle the stream containing the hydrolysis products to the finishing column. The acidic hydrolysis catalyst may be any of those known in the art, preferably a strong acidic cation exchange resin such as that sold as Amberlyst 36® by Rohm and Haas.

The hydrolysis may be carried out, for example, by passing most of the product from the finishing column through a bed of the strong acid cation exchange resin at a temperature of about 10 to about 150° C. at atmospheric pressure and a space velocity of about 10 to about 2000 grams of feed/L of resin per hour.

As stated, the hydrolysis products which comprise mostly acids and alcohols must be removed from the product to maintain its purity. This may be accomplished by the distillation of the product containing hydrolyzed impurities in a separate column or, more desirably, by recycling the hydrolyzed product through the vacuum distillation finishing column. If recycling of the hydrolyzed product is carried out, then the ratio of recycle to the total sidestream product is, for example, about 1:1 to about 10:1.

The purified final product from for example, the vacuum distillation column, from which the hydrolyzed impurities have been removed, is taken as a sidestream from the column and generally contains at least about 99 wt. % of GBL and in many cases as high as about 99.9 wt. % not including the MeGBL's. Furthermore, the MeGBL's and high boiling esters present in such final product are generally present in much lower quantities than in the initial feed to the azeotropic distillation column or in any material between such column and the vacuum distillation finishing column.

In addition to the sidestream product taken from the distillation finishing column as described, a small amount of a residue comprising over 95 wt. % of GBL with minor percentages of MeGBL's and the products of hydrolysis is withdrawn and recycled to the azeotropic distillation column, and an overhead stream comprised primarily of substantial amounts of GBL and water and minor amounts of MeGBL's and products of hydrolysis, are condensed and decanted with most of the overhead in the decanter recycled as reflux to the column and a minor amount including the lower layer withdrawn and burned for fuel.

An important source of the GBL-containing feed to the azeotropic distillation column is a heavy residue from the purification of the products of the liquid phase oxidation of n-butane with molecular oxygen, such residue containing from about 1 to about 70 wt. % of GBL, about 1 to about 30 wt. % of n-butyric acid (HBu) about 1 to about 20 wt. % of other compounds having boiling points near or lower than GBL, and about 1 to about 50 wt. % of compounds having boiling points higher than GBL, often including about 1 to 20 wt. % of succinic anhydride. This residue is generally subjected to a vacuum evaporation step using, for example, a falling film evaporator or a rotary vacuum evaporator operating at a temperature of, for example, about 50 to about 300° C. and a pressure of, for example, about 1 to about 500 mm Hg absolute. The evaporation step yields an overhead product containing, for example, about 10 to about 50 wt. % of GBL, about 1 to about 50 wt. % of butyric acid, and about 1 to about 30 wt. % of other compounds having boiling points near or lower than GBL; and a residue often containing heavy metals, succinic acid and succinic anhydride among other compounds having higher boiling points than GBL, which is generally burned for fuel.

Since succinic anhydride has a melting point of 120° C., it tends to solidify and foul equipment downstream of the vacuum evaporation step if allowed to remain in the overhead from the vacuum evaporation step in any significant quantity. To prevent this, the evaporator is preferably operated to allow about 1 to about 20 wt. % of GBL to remain in the residue which, in effect, substantially prevents much of the succinic anhydride in the feed from vaporizing and leaving the evaporator as part of the overhead.

Since the presence of butyric acid in the GBL-containing feed to the azeotropic distillation column would interfere with the separation process, it is necessary to remove the butyric acid from the overhead of the vacuum evaporator before the GBL-containing composition can be fed to the column. This may be accomplished by subjecting the overhead from the evaporator to the fractional distillation, e.g., in a HBu removal column containing, for example, about 10 to about 100 trays wherein the base temperature is in the range, for example, of about 170 to about 250° C. and the overhead temperature is about 100 to about 190° C., at atmospheric pressure and a reflux to distillate ratio of about 0.5 to about 1.0. The bulk of the HBu in the feed is removed in the column overhead which contains, for example, about 10 to about 99 wt. % of HBu, whereas most of the GBL in the feed is in the base product which contains, for example, about 50 to about 99 wt. % GBL and which is the feed to the azeotropic distillation column as previously described.

Another component of the overhead of the HBu removal column is acetic acid which may be present in the range, for example, of about 0.1 to about 20 wt. %. This amount is 2–3 times the amount in the overall feed to the process, e.g., the residue stream fed to the vacuum evaporator as previously described. The additional acetic acid originates from Michael adducts formed in earlier processing steps. Such adducts are known to decompose at elevated temperatures, e.g., that at the base of the butyric acid removal column, to form acetic acid and olefinic compounds, e.g., acrylic or crotonic acid, or their esters which under certain circumstances tend to polymerize in the HBu removal column, the trays of which may become plugged or fouled by the resulting polymer. To avoid this, a small amount of an inhibitor of the polymerization of acrylic acid, e.g. phenothiazine (PTZ) may be added to the top of the column, e.g. enough to maintain a concentration of about 50 to about 100 wt. % in the reflux.

Another source of GBL-containing feed to the azeotropic distillation column is compositions of varying GBL content resulting from the preparation of GBL by the Reppe reaction of acetylene and formaldehyde.

The purification steps described hereinbefore may be operated as continuous, semi-continuous, or batch operations, separately or together. However, it is preferred that the azeotropic distillation of the invention and any of the other described operations found to be desirable in the production of pure GBL, be carried out as a continuous, integrated, overall process.

EXAMPLE

The following example further illustrates the invention and describes, with reference to the drawing, the preparation of specification grade GBL from a heavy GBL-containing residue obtained as a result of the purification of products of the liquid phase oxidation of n-butane with molecular oxygen, including the azeotropic distillation of a GBL-containing stream, utilizing n-octane as azeotroping agent. The residue contains 26 wt. % GBL, 0.71 wt % MeGBL's, 18 wt. % HBu, 0.21 wt. acetic acid 2.54 wt. % succinic acid and the remainder a large variety of compounds, mostly unidentified, and is fed through line 1 to rotary vacuum evaporator 2 which operates at a pressure of 0.75–3 mm Hg absolute at 108–109° C. and a residence time of about 77 min. The residue containing 2 wt. % of GBL, 5 wt. % of succinic anhydride, and the remainder largely unidentified heavy metals and compounds having higher boiling points than GBL, is taken off through line 3 and burned for fuel, and the overhead comprising 42 wt. % GBL, 1.2 wt. % of MeGBL's, 25 wt. % of HBu, 0.25 wt. % of acetic acid, 0.85 wt. % of crotonic acid, 0.31 wt. % of furanone, 1.8 wt. % of succinic anhydride and the remainder mostly unidentified compounds having boiling points near or lower than GBL, is fed through line 4 to an intermediate tray of HBu removal column 5 which is a 40 tray, 2 inch Oldershaw column operating at a base temperature of about 213° C., an overhead temperature of 165° C., a pressure of 1 atmosphere and a reflux ratio of 0.58. An amount of polymerization inhibitor phenothiazine (PTZ) is added to the top of the column through line 6 to maintain a concentration of PTZ in the reflux of about 50 ppm.

The overhead from HBu removal column 5 containing 66 wt. % of HBu, 0.79 wt. % of GBL, 2.81 wt. % of acetic acid, 3.19 wt. % of acrylic acid, 3.23 wt. % of crotonic acid with the remainder mostly unidentified compounds having boiling points lower than GBL, is withdrawn from line 7 and sent to HBu recovery, while the base product from column 5 containing 63 wt. % of GBL, 2 wt. % of MeGBL's, 0.5 wt. % of furanone, and 0.2–0.5 wt. % of crotonic acid, withdrawn through line 7A is combined with the base product from vacuum distillation finishing column 22 (hereinafter described) in line 29, with the combined stream being fed through line 8 to azeotropic distillation column 9.

Since the mass of the material fed to HBu removal column 5 is about four times the amount of overhead withdrawn from the column, it can be calculated that the amount of acetic acid leaving the column is more than twice as much as that entering the column. Moreover, significantly greater amounts of olefinically unsaturated compounds acrylic acid, crotonic acid and furanone leave the column than enter it. An assumption can therefore be made that the additional acetic acid and unsaturated compounds are formed as a result of the thermal decomposition of Michael adducts in the feed which occurs at a temperature of about 213° C. at the base of the column. This is confirmed by the occurrence of fouling of the top of the column by a substance resembling polymers of acrylic and/or crotonic acids. Such fouling is minimized or prevented by the addition of PTZ inhibitor to the column through line 6 as previously described.

Azeotropic distillation column 9 is constructed of 2 inch Oldershaw sections totaling 40 trays. The GBL-containing feed to column 9, previously described, is fed to tray 20 of the column, while the bulk of azeotroping agent n-octane containing 1.2 wt. % of dissolved GBL, which is the top layer in decanter 10 (hereinafter described) is recycled by way of lines 11 and 12 onto tray 25 of column 9, with a small amount of n-octane, i.e., only large enough to maintain liquid on the top trays of the column, being fed as reflux through lines 11 and 13 to the top of the column. The weight ratio of n-octane to feed entering column 9 is in the range of 18:1 to 23:1 and the column operates at atmospheric pressure and temperatures of 217° C. in the reboiler, 132° C. where the recycled n-octane is introduced, 127° C. at tray 20 where the feed enters and 125° C. at the top of the column. The trays above the octane recycle point are filled mostly with octane and those below the feed point are filled primarily with high boiling material.

The distillate from the top of column 9 including an azeotrope of GBL and n-octane, flows through line 14 to decanter 10, where it is cooled by chilled water, with the distillate settling into two phases, the top phase being primarily n-octane containing 1.2 wt. % of dissolved GBL which is fed back to column 9 as recycle and reflux through line 11 and then through lines 12 and 13 respectively, as described, and the bottom phase being a crude GBL containing 79–83 wt. % GBL, 0.4–0.9 wt. % MeGBL's, 0.5–0.7 wt. % of furanone, 0.9–1.3 wt. % of crotonic acid, 1.9–2.5 wt. % of n-octane, and the remainder various mostly unidentified compounds. The substantially lower weight percent of MeGBL's in the crude GBL product from azeotropic distillation column 9 as compared with that in the feed to such column indicates the effectiveness of the azeotropic distillation process of this invention in reducing the content of the MeGBL's in the GBL product despite the closeness of the boiling points of GBL and the MeGBL's.

A small amount of residue from azeotropic distillation column 9, containing 26.8 wt. % of GBL, 2.8 wt. % of MeGBL's, 7.5 wt. % succinic anhydrids and the remainder various mostly unidentified compounds, is withdrawn through line 15 and recycled to vacuum evaporator 2.

The crude GBL product from azeotropic distillation column 8 obtained as the lower liquid layer in decanter 10 is fed through line 16 to the top of hydrogenation reactor 17 which is a 2 foot section of 2 inch stainless steel pipe packed with a 20 inch bed of 0.5% Pd on carbon hydrogenation catalyst, operating at a hydrogen pressure of 85 psig, a temperature of 152–154° C., a hydrogen feed rate of 194 SCFI/1000 lb feed fed through line 17A to the bottom of reactor 17, a hydrogen vent rate of 32 SCF/1000 lb feed flowing through line 17B from the top of reactor 17 and a hydrogen consumption rate of 191 SCF/1000 lb feed. The hydrogenated product is withdrawn from the bottom of reactor 17 through line 18 and contains 84 wt. % of GBL, 0.5 wt. % of MeGBL's, 7 wt. % of saturated organic acids, 0 wt. % of furanone, 0–0.02 wt. % of crotonic acid, 1.7–2.5 wt. % of n-octane and the remainder various other compounds, most of which are unidentified as to formula but have been determined to have boiling points lower than that of GBL. The substantial elimination of furanone and crotonic acid from the hydrogenated product is an indication that most of the other olefinically unsaturated impurities, including those which cause the development of undesirable color in the GBL product, have also been eliminated.

The hydrogenated product from reactor 17 flowing through line 18 is combined with the hydrolyzed product from hydrolyzer 19 (discussed hereinafter) in line 20 to produce a stream containing 97.5 wt. % GBL, 0.5 wt. % MeGBL's, 1.75 wt. % water, 0.17 wt. % of high boiling esters and the remainder small amounts of other compounds including acid and alcohol hydrolysis products formed in hydrolyzer 19. Such stream is fed through line 21 to tray 35 of vacuum distillation finishing column 22 which is a 50 tray, 2 inch Oldershaw column operating at a pressure of 100 mm Hg absolute and a temperature of 98° C. at the top tray and a pressure of 148 mm Hg absolute and a temperature of 148° C. at the bottom tray. The feed point at tray 35 is at a pressure of 111 mm Hg absolute and a temperature of 138° C. The main product from the column is withdrawn as a sidestream through line from tray 10 which is at a pressure of 131 mm Hg absolute and a temperature of 143° C., and is specification grade GBL containing 99.5 wt. % of GBL, 0.45 wt. % of MeGBL's, 0.02 wt. % of water and 0.04 wt. % of high boiling esters, i.e., having boiling points higher than that of GBL.

To accomplish the reduction of high boiling esters in the product from 0.17 wt. % present in the feed to finishing column 22 to 0.04 wt. % in the product from the column, about ¼ of the product stream in line 23 is withdrawn as final product, while ¾ is mixed with 2.5 wt. % of water and is passed through line 24 into the top of hydrolyzer 19, containing 75 grams of dry Amberlyst 36 acidic cationic exchange resin having a volume of 0.10 L as hydrolysis catalyst, the hydrolyzer operating at about 70° C. and a space velocity of 900 g/l-hr. The hydrolyzed product from which substantially all high boiling esters have been removed, but which now contains hydrolysis acids and alcohols, is then recycled through 20 to finishing column 22 where the hydrolysis products are substantially removed. The hydrolysis and recycling of part of the sidestream product to finishing column 22 at a fairly high ratio of hydrolyzed and recycled product to withdrawn product, e.g. 3:1, accomplish a substantial steady state reduction of high boiling esters present in the feed to finishing column 22 by means of hydrolysis and the removal of the resulting hydrolysis products.

In addition to the main sidestream product, overhead vapors from the top of finishing column containing 27.6 wt. % GBL, 0.14 wt. % of MeGBL's, 68 wt. % of water, 2.5 wt. % of n-octane and the remainder other compounds including some hydrolysis product formed in hydrolyzer 19, are condensed in line 25, the resulting liquid distillate collected in decanter 26 and the bulk of the distillate returned as reflux to the top of finishing column 22 through line 27 at a reflux/distillate ratio of 81.4. That portion of the distillate not returned to the column as reflux is withdrawn from decanter 26 through line 28 and is burned for fuel.

Also obtained from finishing column 22 is a residue stream comprising 98.2 wt. % of GBL, 0.5 wt. % of MeGBL's, 0.02 wt. % of water, and 1.3 wt. % of other compounds, some of which are acid and alcohol hydrolysis products formed in hydrolyzer 19. The residue is recycled through line 29 as feed to azeotropic distillation column 9.

We claim:

1. A process of recovering γ-butyrolactone (GBL) from a mixture containing GBL and other heavy organics having atmospheric boiling points of at least about 130° C. comprising subjecting said mixture to azeotropic distillation in the presence of a $C_8$–$C_{10}$ hydrocarbon as an azeotroping agent, condensing an azeotrope of GBL and said hydrocarbon as a distillate which forms immiscible GBL-rich and hydrocarbon-rich phases, and separating said hydrocarbon-rich phase from said GBL-rich phase by phase separation and/or decantation.

2. The process of claim 1 wherein said hydrocarbon is n-octane.

3. The process of claim 1 wherein said hydrocarbon-rich phase is recycled to the azeotropic distillation.

4. The process of claim 1 wherein said mixture containing GBL and subjected to azeotropic distillation also comprises methyl-γ-butyrolactones (MeGBL's) which are separated from GBL using said hydrocarbon azeotroping agent.

5. The process of claim 1 wherein the GBL-rich phase contains olefinically unsaturated impurities and is subjected to a hydrogenation treatment to eliminate or reduce the unsaturation of said impurities.

6. The process of claim 5 wherein said hydrogenation is catalyzed by palladium.

7. The process of claim 1 wherein the GBL-rich phase is subjected to a finishing treatment for the purpose of removing additional impurities having lower and higher boiling points than GBL.

8. The process of claim 7 wherein the purified GBL from the finishing treatment contains a small amount substantially less than said GBL of high boiling esters, all or part of said purified GBL is subjected to hydrolysis conditions to hydrolyze said esters and the material subjected to hydrolysis conditions is fractionally distilled to remove hydrolysis acids and alcohols.

9. The process of claim 8 wherein said hydrolysis conditions include contact with a strong acidic cationic exchange resin as hydrolysis catalyst.

10. The process of claim 8 wherein said finishing treatment is a vacuum fractional distillation step and said purified GBL subjected to hydrolysis conditions is fractionally distilled by recycling it to said finishing treatment to remove said hydrolysis acids and alcohols.

11. The process of claim 1 wherein said mixture subjected to azeotropic distillation is obtained from a residue resulting from the purification of products of the liquid phase oxidation with molecular oxygen of n-butane, said residue having been subjected to a vacuum evaporation treatment to remove very heavy ends having the highest boiling points in said residue, and the overhead from the vacuum evaporation treatment which has an increased percentage of GBL as compared with the feed to the vacuum evaporation treatment having been subjected to a fractional distillation treatment to remove butyric acid and other light ends as overhead, with the residue from the latter distillation treatment which has a still further increased percentage of GBL being the feed mixture to the azeotropic distillation.

12. The process of claim 1 wherein said hydrocarbon azeotroping agent is n-octane, n-nonane, or n-decane.

13. The process of claim 1 wherein said other heavy organics include about 0.1 to about 50 wt. % of MeGBL's and about 0.1 to about 50 wt. % of esters having atmospheric boiling points of about 150° C. to about 250° C.

14. The process of claim 11 wherein said residue subjected to said vacuum evaporation treatment contains from about 1 to about 70 wt. of GBL.

* * * * *